United States Patent [19]

Stephens, deceased et al.

[11] Patent Number: Plant 6,262

[45] Date of Patent: Aug. 30, 1988

[54] ROSE PLANT NAMED STEBIGPU

[76] Inventors: Patrick N. Stephens, deceased, late of Te Awamutu, New Zealand; by Patricia I. J. Stephens, legal representative, 139 Kihi Kihi Road, Te Awamutu, New Zealand

[21] Appl. No.: 895,289

[22] Filed: Aug. 11, 1986

[51] Int. Cl.[4] ..... A01H 5/00

[52] U.S. Cl. ..... Plt./19

[58] Field of Search ..... Plt./11, 19, 21

*Primary Examiner*—Robert E. Bagwill

*Attorney, Agent, or Firm*—Vincent G. Gioia

[57] ABSTRACT

A new large, heavily petalled reddish purple hybrid tea rose variety.

1 Drawing Sheet

The present invention relates to a new and distinct variety of rose plant of the hybrid tea rose class, which was originated by my crossing as seed parent an unnamed, unpatented seedling of my creation and as pollen parent the rose known as "Purple Splendor". The varietal denomination of this new rose is "Stebigpu".

Among the novel characteristics possessed by this new variety which distinguish it from its parents and all other varieties of which I am aware are its large, heavily petalled reddish purple flowers borne on a vigorous, tall growing plant with dark green foliage very resistant to disease. Flowers are long lasting on the plant or after cutting. Asexual reproduction by budding of the new variety as performed in Clackamas County, Oreg. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "184A" is plate 184A of The Royal Horticultural Society Colour Chart.

Parentage: Seedling.

*Seed parent.*—Unnamed seedling.

*Pollen parent.*—"Purple Splendor".

Class: Hybrid Tea.

The following observations are made of specimens grown outdoors in Clackamas County, Oreg., during the month of September.

FLOWER

Blooming habit: Continuous.

A. Bud:

(1) *Size.*—Large.

(2) *Form.*—Spiraled.

(3) *Color.*—As sepals divide, buds are near 184A with yellow base at petal attachment.

(4) *Sepals.*—Simple, about as long as bud.

(5) *Peduncle.*—Length — medium. Aspect — straight. Strength — erect. Color — near 153B.

B. Bloom:

(1) *Size.*—Average size when fully expanded — about 5 inches.

(2) *Borne.*—Singly, one to a stem.

(3) *Form.*—Relatively high centered, spiraled, becoming flat upon opening.

(4) *Petalage.*—Number of petals under normal conditions — about 60–70.

(5) *Color.*—As petals unfurl and flower opens, flower color is near Rhodonite red 51A to cardinal red 53C. As flower matures and ages, pronounced purple shading develops to become near 185D to 185C, with lighter tones at outer segments of outer petals; thus shading from deeper tonality at flower centers to lighter shades at outer petal edges, but color variation is slight. General tonality from a distance as flowers age is reddish purple.

C. Petals (1) *Texture.*—Thick.

(2) *Appearance.*—Inside velvety and outside satiny.

(3) *Form.*—Spiraled.

(4) *Arrangement.*—Regularly arranged, imbricated.

(5) *Petaloids in center.*—Few.

(6) *Persistence.*—Drop off cleanly.

(7) *Fragrance.*—Rich rose.

(8) *Lasting quality.*—Very long lasting quality on plant and as cut flower.

REPRODUCTIVE ORGANS

A. Stamens, filaments and anthers:

*Arrangement and color.*—Irregular, profuse. Color — near 15B.

B. Pollen:

*Color.*—Near 15A.

C. Styles: Even, many, near 47A.

D. Stigmas:

*Color.*—Tiny, near 49C.

E. Hips: None observed.

PLANT

A. Form: Upright.

B. Growth: Vigorous.

*Height attained.*—About 6 feet.

C. Foliage: Compound 5 leaflets.

(1) *Size.*—Medium.

(2) *Quantity.*—Abundant, but small.

(3) *Color.*—New foliage: Upper side — near 147B. Under side — near 148C. Old foliage: Upper side — near 147A. Under side — near to 148C.

(4) *Shape.*—Ovoid.

(5) *Texture.*—Upper side is stippled-leathery and under side is glaborous-heavily veined.

(6) *Edge.*—Barely serrate.

(7) *Serration.*—Nearly simple.

(8) *Leaf stem.*—Color — near to 144B. Under side — near 144B.

(9) *Stipules.*—Fancy — heavily bearded.

(10) *Resistance to disease.*—Blackspot — excellent. Mildew — excellent. Rust — excellent.

D. Wood:

(1) *New wood.*—Color — near 147A. Bark — smooth.

(2) *Old wood.*—Color — near 147C. Bark — smooth.

E. Thorns:

(1) *Thorns.*—Quantity (main stalk) — few. Form — recurved. Length — medium. Color — near 168A. Position — irregular.

(2) *Prickles.*—None.

F. Winter hardiness: Very winter hardy.

It is claimed:

1. A new and distinct variety of rose plant of the hybrid tea rose class, substantially as shown and described, characterized particularly by large, heavily petalled reddish purple flowers borne on a vigorous, disease resistant plant and which are long lasting on the plant and as cut flowers.

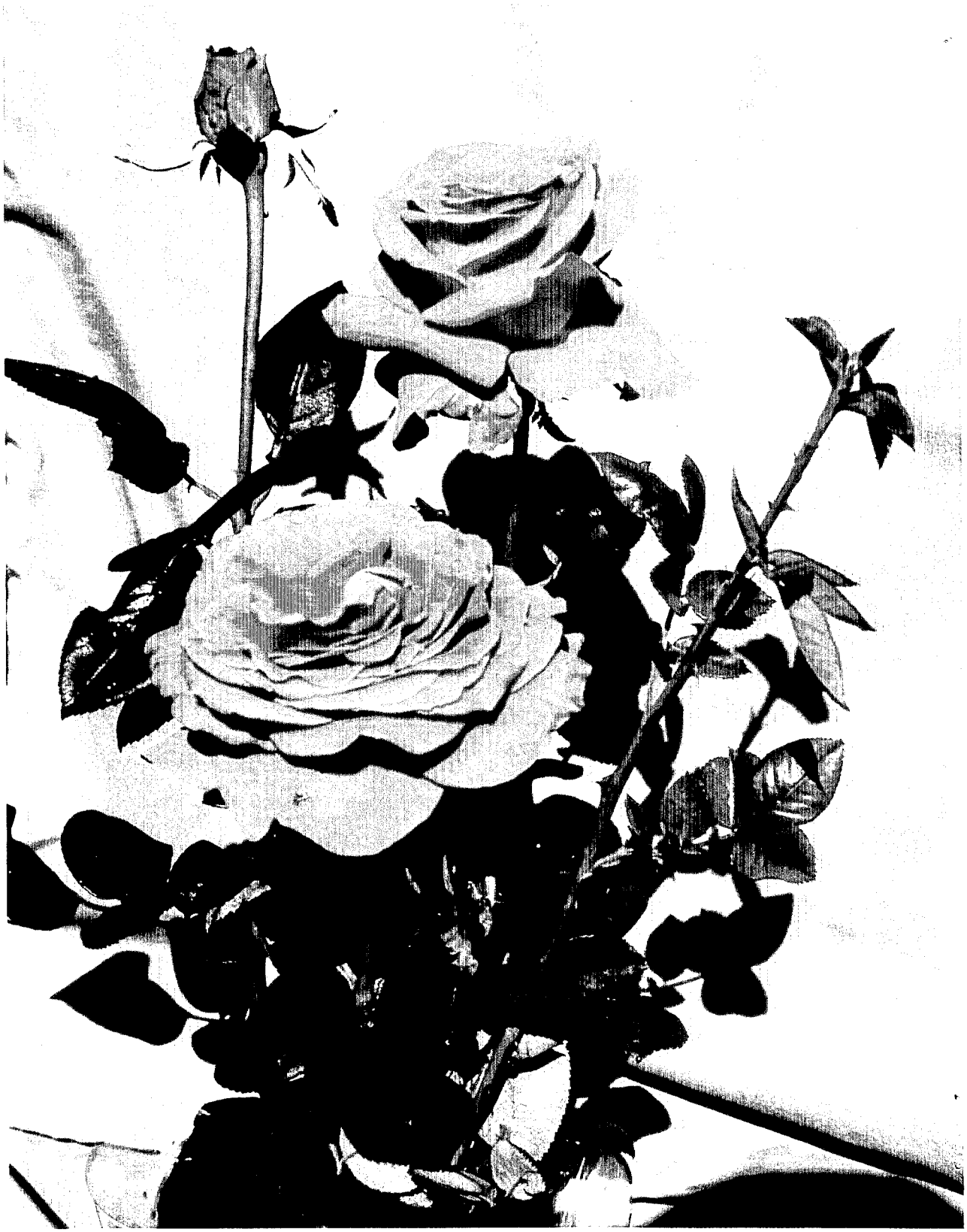

* * * * *